United States Patent
Tadano et al.

(10) Patent No.: US 9,814,480 B2
(45) Date of Patent: Nov. 14, 2017

(54) FORCEPS MANIPULATOR AND FORCEPS SYSTEM COMPRISING FORCEPS MANIPULATOR

(71) Applicant: Tokyo Institute of Technology, Meguro-ku, Tokyo (JP)

(72) Inventors: Kotaro Tadano, Tokyo (JP); Kenji Kawashima, Tokyo (JP); Daisuke Haraguchi, Tokyo (JP)

(73) Assignee: Tokyo Institute of Technology, Tokyo (JP)

( * ) Notice: Subject to any disclaimer, the term of this patent is extended or adjusted under 35 U.S.C. 154(b) by 112 days.

(21) Appl. No.: 14/439,934

(22) PCT Filed: Feb. 12, 2013

(86) PCT No.: PCT/JP2013/053226
§ 371 (c)(1),
(2) Date: Apr. 30, 2015

(87) PCT Pub. No.: WO2014/069003
PCT Pub. Date: May 8, 2014

(65) Prior Publication Data
US 2015/0313619 A1   Nov. 5, 2015

(30) Foreign Application Priority Data

Nov. 1, 2012 (JP) ................................ 2012-241952

(51) Int. Cl.
*A61B 34/30* (2016.01)
*A61B 17/29* (2006.01)
(Continued)

(52) U.S. Cl.
CPC .............. *A61B 17/29* (2013.01); *A61B 34/30* (2016.02); *A61B 34/71* (2016.02); *A61B 2017/00544* (2013.01); *A61B 2034/306* (2016.02)

(58) Field of Classification Search
CPC ......... A61B 34/71; A61B 34/30; A61B 17/29; A61B 17/00234; A61B 2017/00544; A61B 2034/305; A61B 2034/306
See application file for complete search history.

(56) References Cited

U.S. PATENT DOCUMENTS

| 2009/0054733 A1 | 2/2009 | Marescaux et al. |
| 2009/0171374 A1 | 7/2009 | Omori |

(Continued)

FOREIGN PATENT DOCUMENTS

| JP | 2009-50697 A | 3/2009 |
| JP | 2009-160011 A | 7/2009 |

(Continued)

OTHER PUBLICATIONS

International Search Report (PCT/ISA/210) dated May 14, 2013, with English translation (Four (4) pages).

(Continued)

*Primary Examiner* — Tammie K Heller
(74) *Attorney, Agent, or Firm* — Crowell & Moring LLP (57) ABSTRACT

The present invention is intended to improve durability and operability of a forceps manipulator, as well as to facilitate roll motions of the forceps manipulator. In the forceps manipulator, a flexible shaft 34 is connected to a rotating joint unit 26 for transmitting a driving force from a vane motor 40 to the rotating joint unit 26 through throughholes 18a, 22a of machined springs 18b, 22b which respectively constitute flexible first and second joints 18, 22.

5 Claims, 11 Drawing Sheets

(51) Int. Cl.
*A61B 34/00* (2016.01)
*A61B 17/00* (2006.01)

(56) References Cited

U.S. PATENT DOCUMENTS

2009/0182436 A1 7/2009 Ferrara
2010/0030023 A1 2/2010 Yoshie

FOREIGN PATENT DOCUMENTS

JP  2009-527366 A  7/2009
JP     2010-35768 A  2/2010

OTHER PUBLICATIONS

Japanese language Written Opinion (PCT/ISA/237) dated May 14, 2013 (Four (4) pages).
Japanese language International Preliminary Report on Patentability (PCT/IPEA/416 & PCT/IPEA/409) dated Feb. 24, 2015 Six (6) pages).
Japanese language Written Opinion of the International Preliminary Examining Authority (PCT/IPEA/408) dated Sep. 30, 2014 (Six (6) pages).
Hagn, U. et al., "DLR MicroSurge : a versatile system for research in endoscopic telesurgery", International Journal of Computer Assisted Radiology and Surgery, 2009, vol. 5, pp. 183-193 (11 pages).
Xu, K. et al., "System Design of an Insertable Robotic Effector Platform for Single Port Access (SPA) Surgery", The 2009 IEEE/RSJ International Conference on Intelligent Robots and Systems, Oct. 11-15, 2009 St. Louis, USA, pp. 5546-5552, (seven (7) pages).
Haraguchi, D. et al., "Development of Pneumatically-Driven Forceps Manipulator Using Push-Pull Mechanism Made of Superelastic Alloy Wire", The $12^{th}$ International Symposium on Fluid Control, Measurement and Visualization, The Society of Instrument and Control Engineers Symposium on Industrial Applications Systems, 2011, pp. 22-25, with English Abstract (five (5) pages).
Haraguchi, D. et al., "A Prototype of Pneumatically-Driven Forceps Manipulator with Force Sensing Capability Using a Simple Flexible Joint", 2011 IEEE/RSJ International Conference on Intelligent Robots and Systems, Sep. 25-30, 2011, San Francisco, CA, USA, pp. 931-936 (six (6) pages).
Tadano, K. et al., "Development of a Pneumatic Surgical IBIS IV", Development of a Pneumatic Surgical Manipulator IBIS IV, Journal of Robotics and Mechatronics, 2010, vol. 22., No. 2, pp. 179-188 (ten (10) pages).
Haraguchi, D. et al., "Development of a Pneumatically-Driven Forceps Manipulator Using a Flexible Joint (Simplification of the Joint Mechanism and External Force Estimation)," The Japan Fluid Power System Society Ronbunshu, 2012, vol. 43, No. 3, pp. 62-69, with English Abstract (nine (9) pages).

FORCEPS MANIPULATOR AND FORCEPS SYSTEM COMPRISING FORCEPS MANIPULATOR

TECHNICAL FIELD

The present invention relates to a forceps manipulator and a forceps system comprising the forceps manipulator.

BACKGROUND ART

In a surgical robot system, a forceps system comprising a forceps manipulator is practically used. As shown in Hagn, U., et al., DLR MiroSurge: a versatile system for research in endoscopic telesurgery, International Journal of Computer Assisted Radiology and Surgery, Vol. 5, p. 183-193 (2010), 10.1007/s11548-009-0372-4, for example, such a forceps manipulator has an arm with two degrees of freedom inside a human body (three degrees of freedom including a grip), and an arm with four degrees of freedom outside the human body. Such an arrangement is due to a restriction that implementing multiple degrees of freedom is difficult at a tip portion of a thin forceps provided in a forceps manipulator.

In addition, for a forceps manipulator, as also shown in K. Xu, R. Goldman, J. Ding, P. Allen, D. Fowler, and N. Simaan, "System design of an insertable robotic effector platform for single port access (spa) surgery", IEEE/RSJ International Conference on Intelligent Robots and Systems, pp. 5546-5552, 2009, for example, a flexible forceps manipulator is proposed that can bend with four degrees of freedom within the abdominal cavity of a human body. A bending portion of the forceps manipulator is divided into two segments. Each segment is bendable with two degrees of freedom. A bendable elastic body is formed by connecting a plurality of metal plates with a superelastic alloy tube running through the respective centers of the plurality of the metal plates. Further, its bendability is achieved by running through a driving tube or a wire made of superelastic alloy on peripheral portions of the metal plates. An upstream joint constituting one segment is driven by four superelastic alloy tubes, while a downstream joint constituting the other segment is driven by four superelastic alloy wires. The superelastic alloy wires for driving the downstream joint respectively run through inside the superelastic alloy tubes for driving the upstream joint. This gives advantageous effects of allowing for reducing an arrangement space for driving-force transmission components of the forceps manipulator, as well as simplifying kinematic calculations of the forceps manipulator.

Furthermore, for a forceps manipulator, as shown in Haraguchi, D., et al., "Development of Pneumatically-Driven Forceps Manipulator Using Push-Pull Mechanism Made of Superelastic Alloy Wire", for example, a forceps manipulator for laparoscopic surgery is proposed that has a simple flexible bending mechanism suitable for reduction in size. A joint structure of the mechanism is made from only a machined spring molded in one piece. A superelastic alloy wire running through inside this joint structure is operated in a push-pull motion by a pneumatic cylinder, and this allows for bending motions with higher rigidity than an antagonistic driving that utilizes a conventional wire tension. This allows such a joint structure to bend in directions of two degrees of freedom.

Then, as shown in Daisuke Haraguchi, Kotaro Tadano, Kenji Kawashima, A Prototype of Pneumatically-Driven Forceps Manipulator with Force Sensing Capability Using a Simple Flexible Joint, 2011 IEEE/RSJ International Conference on Intelligent Robots and Systems, pp. 931-936, a simple theoretical model is proposed for estimating an external force in the forceps manipulator, which model approximates a flexible joint in the forceps manipulator by a rigid linkage mechanism with two degrees of freedom.

SUMMARY OF THE INVENTION

Problems to be Solved

In the forceps manipulator as shown in Hagn, U., et al., DLR MiroSurge: a versatile system for research in endoscopic telesurgery, International Journal of Computer Assisted Radiology and Surgery, Vol. 5, p. 183-193 (2010), 10.1007/s11548-009-0372-4, the arm located outside the human body is moved up and down as well as right and left, and may stand in the way of an assistant. In addition, if multiple forceps are used, another problem may be caused such as the arms interfering with each other.

In addition, the components of the elastic body shown in K. Xu, R. Goldman, J. Ding, P. Allen, D. Fowler, and N. Simaan, "System design of an insertable robotic effector platform for single port access (spa) surgery", IEEE/RSJ International Conference on Intelligent Robots and Systems, pp. 5546-5552, 2009 are wires and tubes only, then it is contemplated that rigidity of the joint against external forces (especially, torsional moments) may sometimes be insufficient. Further, a joint center requires a superelastic alloy tube as a backbone structure, then is subjected to buckling or breakage when being bent, receiving external forces, or the like. Furthermore, coupling disks are required to secure a range of bending motion, and this may cause the joint itself to become longer, to inhibit compact bending motions. As a solution, thickness of the disk may be decreased, but accordingly this makes a connecting area with the superelastic alloy to be decreased to cause the rigidity of the joint as described above to be decreased. If rigidity and strength of the joints are insufficient, not only the durability of the forceps manipulator, but also the operability of the forceps manipulator may be degraded even with a small external force such as one caused by contacting organs.

In the forceps manipulator as shown in Haraguchi, D., et al., "Development of Pneumatically-Driven Forceps Manipulator Using Push-Pull Mechanism Made of Superelastic Alloy Wire", adopting a machined spring for the main structure of the joint has improved insufficient rigidity of the joint as a problem of the forceps manipulator shown in K. Xu, R. Goldman, J. Ding, P. Allen, D. Fowler, and N. Simaan, "System design of an insertable robotic effector platform for single port access (spa) surgery", IEEE/RSJ International Conference on Intelligent Robots and Systems, pp. 5546-5552, 2009. However, because the joint has only two degrees of bending freedom, an additional four degrees of bending freedom need to be implemented by a retention manipulator outside the human body. The retention manipulator generally requires a larger moving space as compared to a tip portion, and this may cause a problem of interferences, while the retention manipulator is in operation, such as manipulators colliding with each other. Accordingly, a restriction may exist in the number of instruments used at the same time and in arranging those instruments, and additionally, in the forceps manipulator, when performing a roll operation of the tip, for example, all four cylinders need to be operated in a coordinated manner and this may sometimes cause degradation in controlling positions.

In addition, estimating forces with three degrees of freedom is not described in Daisuke Haraguchi, Kotaro Tadano, Kenji Kawashima, A Prototype of Pneumatically-Driven Forceps Manipulator with Force Sensing Capability Using a Simple Flexible Joint, 2011 IEEE/RSJ International Conference on Intelligent Robots and Systems, pp. 931-936.

In view of the above problems, the present invention is intended to provide a forceps manipulator and a forceps system comprising the forceps manipulator, which allow for improving durability and operability of the forceps manipulator, as well as facilitating roll motions of the forceps manipulator.

Solution to Resolve Problems

In order to achieve the above objective, a forceps system comprising a forceps manipulator according to the present invention is configured to include a forceps manipulator including: a rotating joint unit that rotates a gripping unit having a forceps; a plurality of flexible multi-degree-of-freedom joints that are respectively provided with throughholes along the axial direction and connected to the rotating joint unit; and a driving unit that drives the rotating joint unit via flexible driving-force transmitting members which are respectively inserted into the throughholes of the plurality of the multi-degree-of-freedom joints, and a control unit that controls the driving unit of the forceps manipulator so as to control posture of the gripping unit.

The forceps manipulator according to the present invention is configured to include: a rotating joint unit that rotates a gripping unit having a forceps; a plurality of flexible multi-degree-of-freedom joints that are respectively provided with throughholes along the axial direction and connected to the rotating joint unit; and a driving unit that drives the rotating joint unit via flexible driving-force transmitting members which are respectively inserted into the throughholes of the plurality of the multi-degree-of-freedom joints.

Advantageous Effects of the Invention

According to the forceps manipulator and the forceps system comprising the forceps manipulator of the present invention, the driving unit of the forceps manipulator rotates the rotating joint unit via the flexible driving-force transmitting member which are respectively inserted into the throughholes of the plurality of the multi-degree-of-freedom joints, thereby improving durability and operability of the forceps manipulator and facilitating roll motions of the forceps manipulator.

EMBODIMENTS OF THE INVENTION

Hereinafter, embodiments of the invention will be described. It should be noted that in the text of the present specification, an alphabetical character having a hat symbol will be referred to as "(alphabetical character) hat" and a character having an over-dot will be referred to as "(alphabetical character) over-dot."

Figure 2:
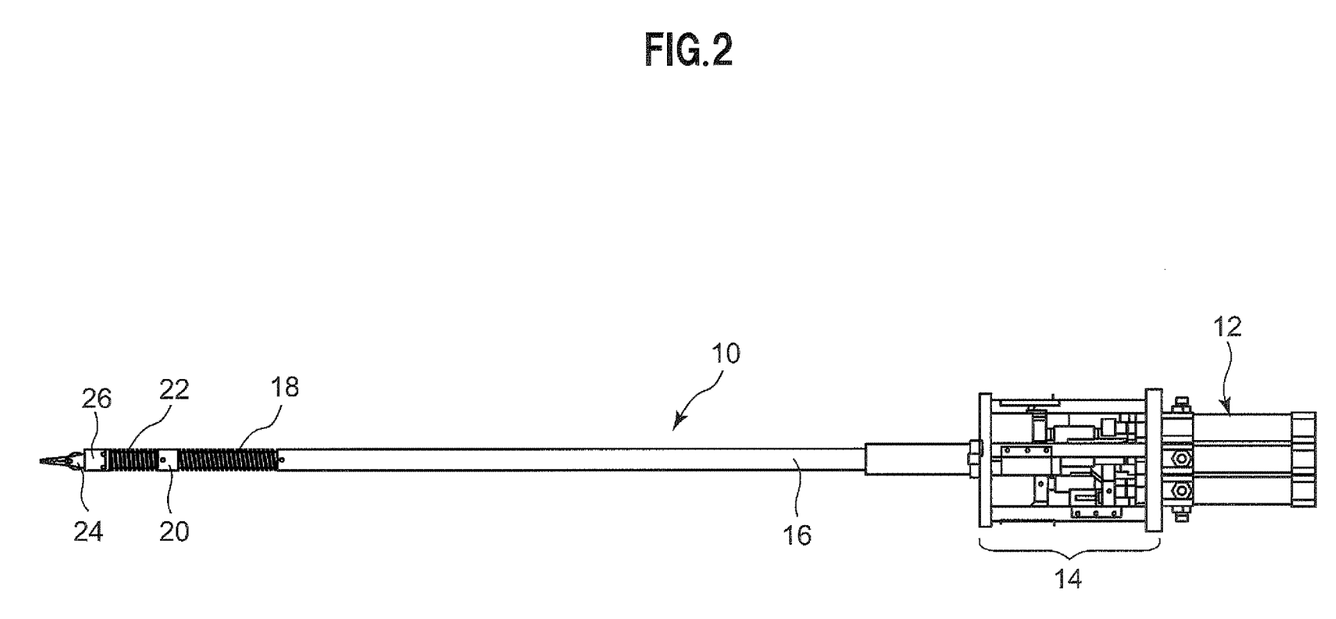
FIG. 2 is an exterior view of the forceps manipulator shown in FIG. 1.

FIG. 2 shows an exterior view of a forceps manipulator used in an embodiment of a forceps system comprising the forceps manipulator according to the present invention.

In FIG. 2, a forceps manipulator 10 is configured to include, as main components: a joint driving unit 12 composed of eight air cylinders 12a1 to 12a8; a connector unit 14 that connects respective piston rods of the joint driving unit 12 with a plurality of wires and tubes to be described later; a gripping unit 24 that is configured to include a forceps; a rotating joint unit 26 that is connected to a base end of the gripping unit 24; a second joint 22 that is connected via a ball bearing 22BE to a base end of the rotating joint unit 26; a first joint 18 that is connected to the second joint 22 via a fitting hole unit 18ff which is fitted into the fitting cylinder 22mf at one end of the second joint 22 for fixing by screwing; and a driving-force transmitting unit 16 that is connected to the connector unit 14 at one end and fitted into a fitting cylinder 18mf of the first joint 18 at the other end to movably support a plurality of wires and tubes running through the first joint 18.

Figure 1:
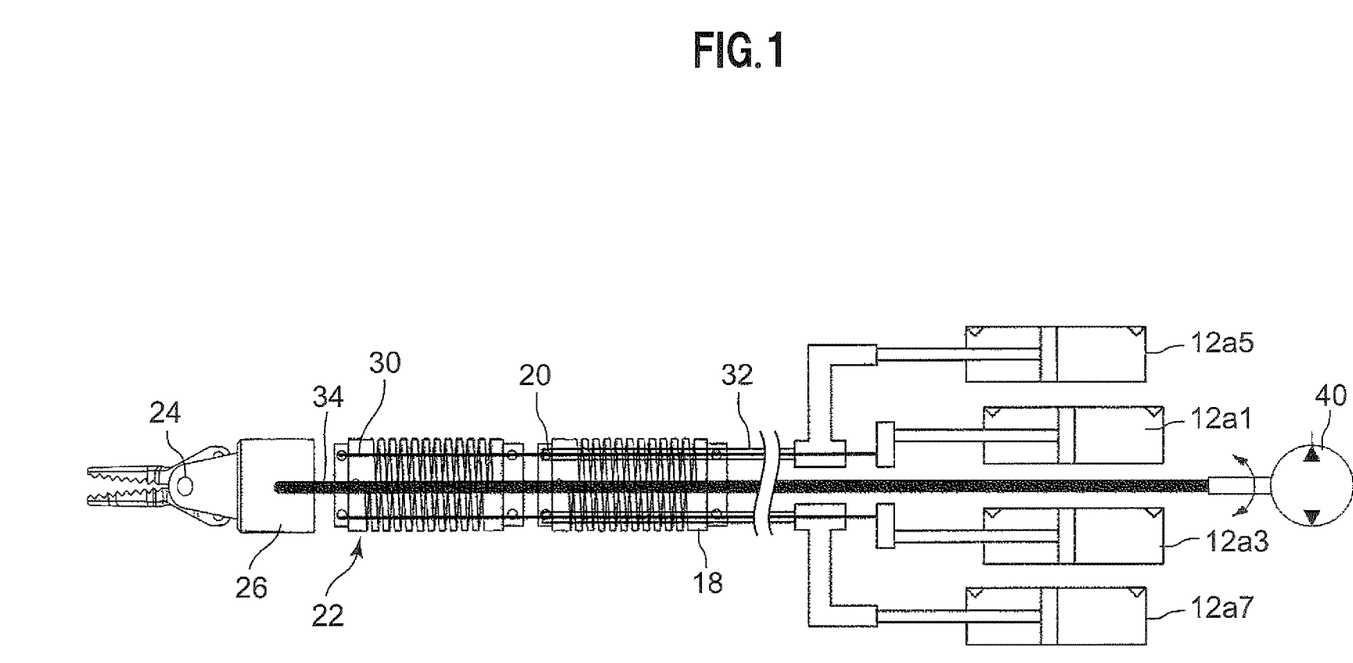
FIG. 1 is a diagram schematically showing a configuration of an embodiment of a forceps manipulator according to the present invention.
Figure 9:
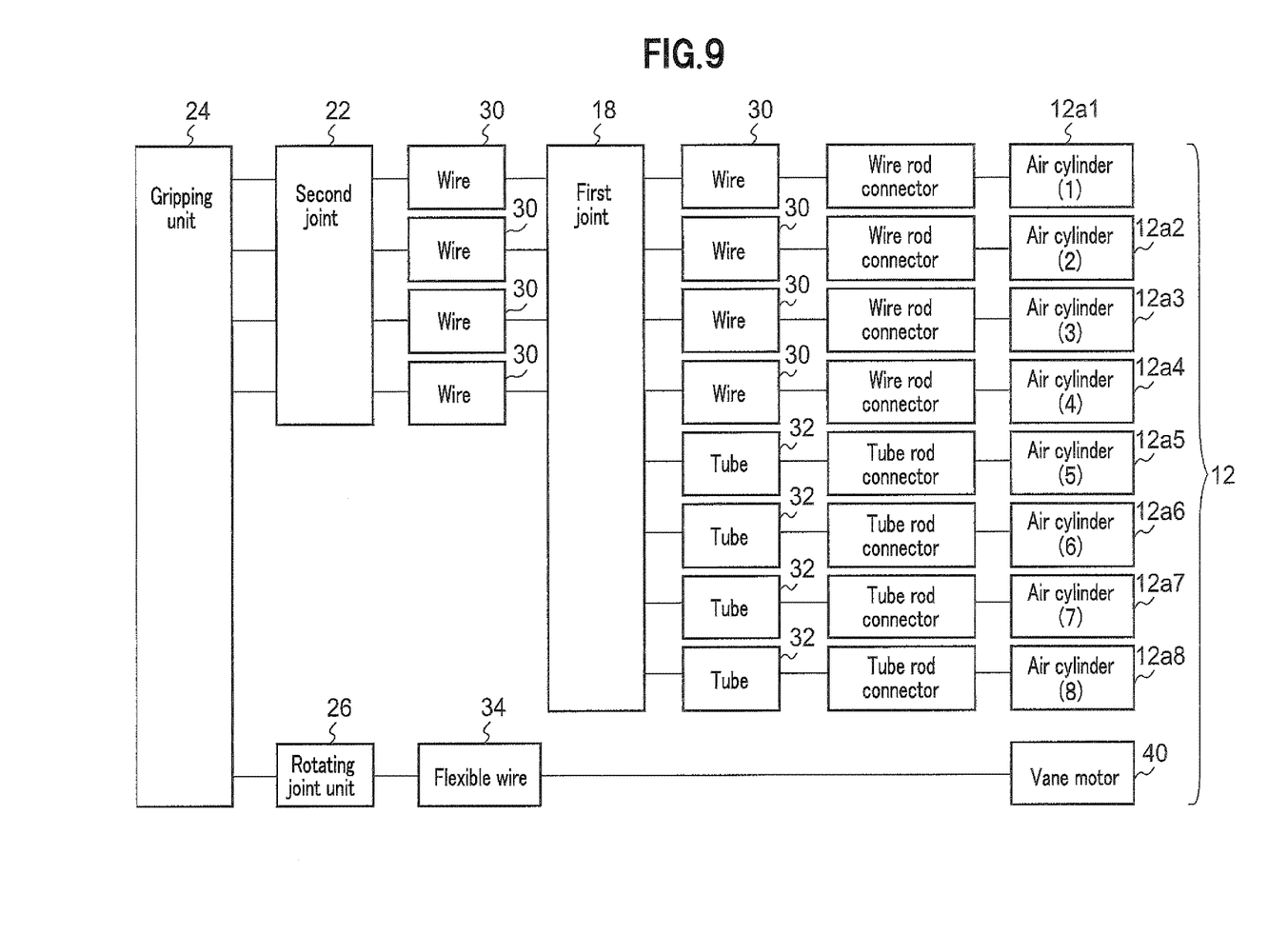
FIG. 9 is a block diagram to be used in a description of a transmission path of the driving force in the embodiment shown in FIG. 1.

The eight air cylinders 12a1 to 12a8 are supported by a support plate 42 in the connector unit 14. Respective piston rods 12L of the air cylinders 12a1 to 12a8 project into the connector unit 14 so as to be perpendicular to an end surface of a support plate 42. Air cylinders 12a1 to 12a4 (see FIG. 9) of the eight air cylinders 12a1 to 12a8 are intended to move respective wires 30 back and forth, which are connected to the piston rods 12L via a wire rod connector 38 (see FIG. 3). As shown in FIG. 1, the air cylinder 12a1 and the air cylinder 12a3 are arranged to face with each other.

Also, the air cylinder 12a2 and the air cylinder 12a4 are arranged to lace with each other.

Figure 3:
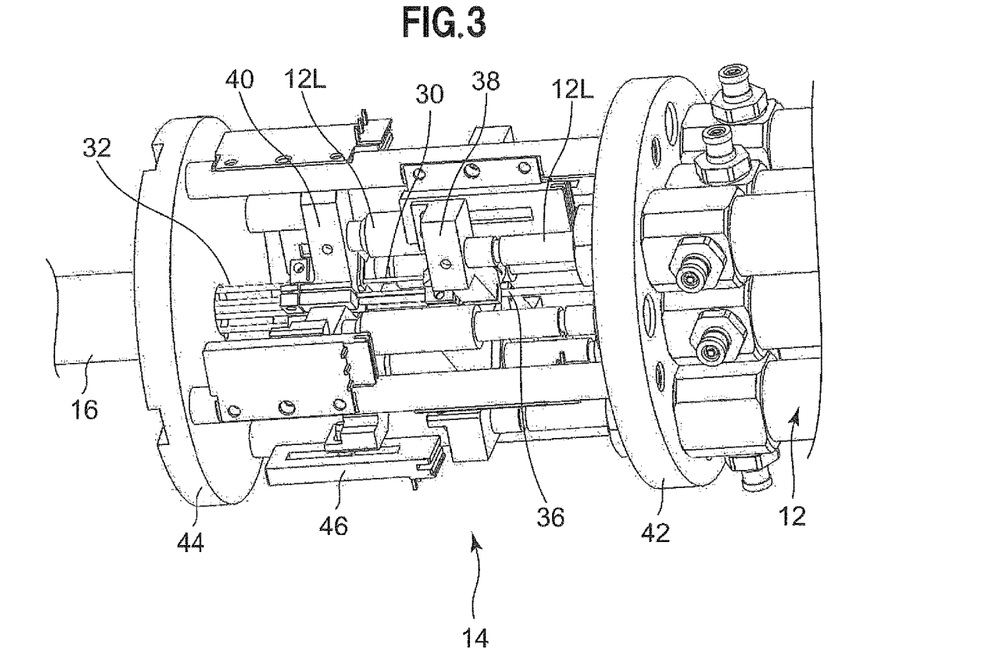
FIG. 3 is a perspective view showing a structure of a connector unit in the embodiment shown in FIG. 1.

In addition, the remaining air cylinders 12a5 to 12a8 (see FIG. 9) are intended to move respective tubes 32 back and forth, which are connected to respective piston rods 12L via a tube rod connector 40 (see FIG. 3). The air cylinder 12a5 and the air cylinder 12a7 are arranged to face with each other. Also, the air cylinder 12a6 and the air cylinder 12a8 are arranged to face with each other.

Amounts of stroke and the velocities of the respective piston rods 12L of the air cylinders 12a1 to 12a8 are controlled, while being driven, by a pneumatic controller 72 (see FIGS. 11 and 12) to be described later.

As shown enlarged in FIG. 3, the connector unit 14 is configured to include: support plates 42 and 44 that are arranged to face with each other at a predetermined distance and are connected with a plurality of shafts; a plurality of wire rod connectors 38 that are disposed between the support plates 42 and 44 to connect the piston rods 12L and ends of the wires 30; and a plurality of tube rod connectors 40 that are disposed between the support plates 42 and 44 to connect the piston rods 12L and ends of the tubes 32. A plurality of potentiometers 46 are provided adjacent to respective wire rod connectors 38 and the tube rod connectors 40, to detect respective amounts of movement of the wires 30 and the tubes 32. The plurality of the potentiometers 46 are intended to supply output detection signals Si, respectively, to a control unit 60 to be described later. The tubes 32 and the wires 30 are respectively made of superelastic alloy, for example. This connection, in which the tubes 32 and the wires 30 have structures of not bending, can minimize a sliding friction force of a mechanism to contribute to improve controllability as well as accuracy of estimating an external force, as will be described later.

The support plate 42 additionally supports a vane motor 40 (see FIG. 9) that rotates the rotating joint unit 26 via a flexible shaft 34. The vane motor 40 is controlled by the control unit 60 to be described later.

Figure 4:
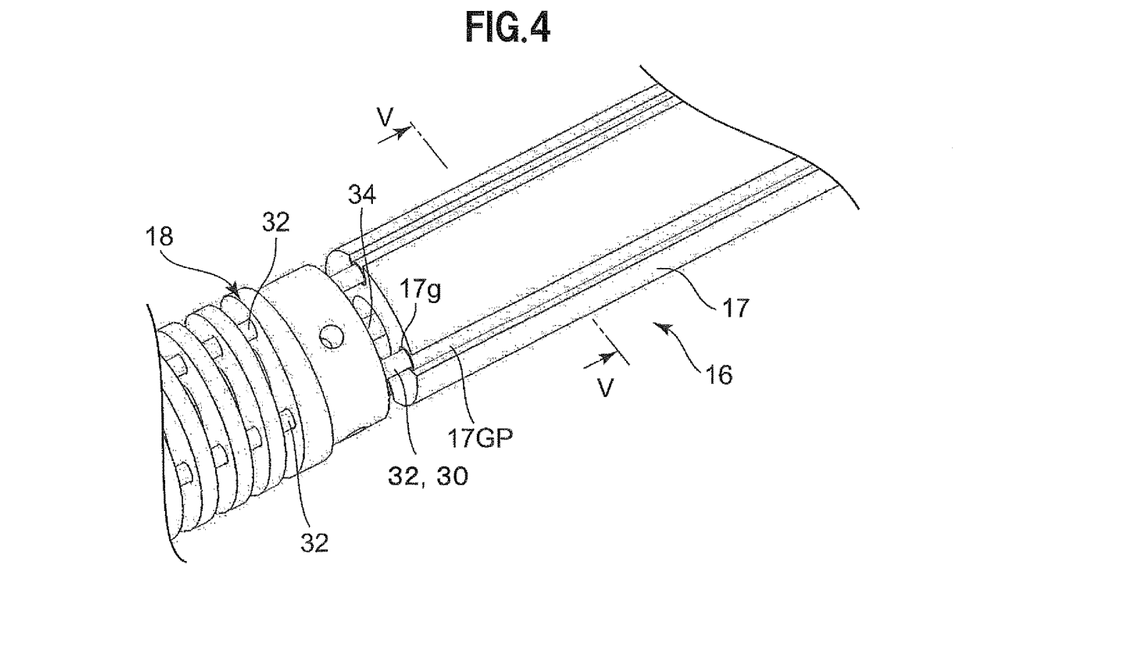
FIG. 4 is a perspective view showing an enlarged part of a driving-force transmitting portion of the forceps manipulator in the embodiment shown in FIG. 1.
Figure 5:
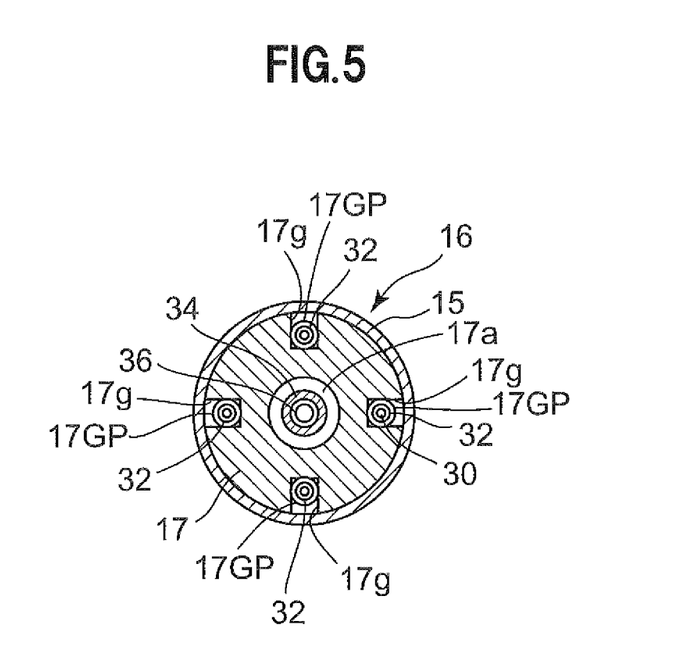
FIG. 5 is a partial cross-sectional view taken along a line V-V in FIG. 4.

One end of a cylindrical pipe 15 of the driving-force transmitting unit 16 is connected to the support plate 44, while the other end thereof extends along the axial direction to fit into a fitting cylinder 18mf of the first joint 18 for connection by screwing. The other end of the cylindrical pipe 15 is provided, along a circumferential direction, with a plurality of throughholes in association with respective screw holes of the fitting cylinder 18mf of the first joint 18. This allows for screwing small screws (not shown) into the screw holes of the fitting cylinder 18mf via the throughholes. As shown in FIGS. 4 and 5, the driving-force transmitting unit 16 is configured to include, as main components: a separator 17 that supports the wires 30 and the tubes 32 as described above; and a cylindrical pipe 15 that accommodates the separator 17 inside the cylindrical pipe 15.

The elongated separator 17 having a circular cross-section is provided with a throughhole 17a, in the center of the section, for inserting a flexible shaft 34 and an air supply tube 36. The separator 17 is formed with grooves 17g, on the outer periphery thereof, along the circumferential direction at four positions equally spaced for arranging guide pipes 17GP made of stainless steel. The tube 32s in a cylindrical shape and the wires 30 having a circular cross-section are movably arranged inside the respective guide pipes 17GP. The wire 30 is movably arranged on the inner periphery of the tube 32 with a predetermined gap.

The wire 30 and the tube 32 are required not to cause buckling for a push-pull operation, especially inside the driving-force transmission unit 16, with respect to a compression force. With the tubes 32 and the wires 30 running through the guide pipes 17GP, ideal straight paths are secured. Further, the guide pipes 17GP are firmly fixed in the grooves 17g of the separator 17, for preventing buckling of the guide pipes 17GP themselves.

Figure 8A:
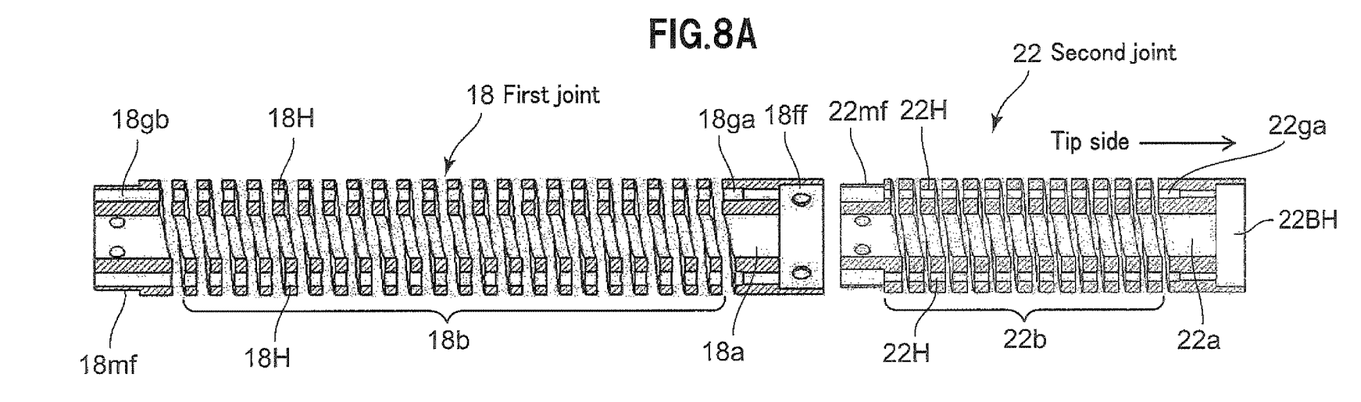
FIG. 8A is a sectional view showing machined springs constituting the first and second joints in the embodiment shown in FIG. 1.

The first joint 18 has a flexible structure, for example, formed with a machined spring 18b, as shown in FIG. 8A. The machined spring 18b can be obtained, for example, by cutting a cylindrical metal material to form a spiral shape using laser processing or the like. The fitting hole unit 18ff, which is integrally formed at one end of the machined spring 18b, is formed with throughholes 18ga, to which one end of the tube 32 having the wire 30 inserted inside is adhered, at four places in association with the grooves 17g of the separator 17 as described above. The fitting cylinder 18mf, which is integrally formed at the other end of the machined spring 18b, is formed with throughholes 18gb, in which the tube 32 for inserting the wire 30 is inserted, at four places in association with the grooves 17g of the separator 17 as described above.

A flexible shaft 34 is inserted in a throughhole 18a at the cross-sectional center of the machined spring 18b.

Figure 6:
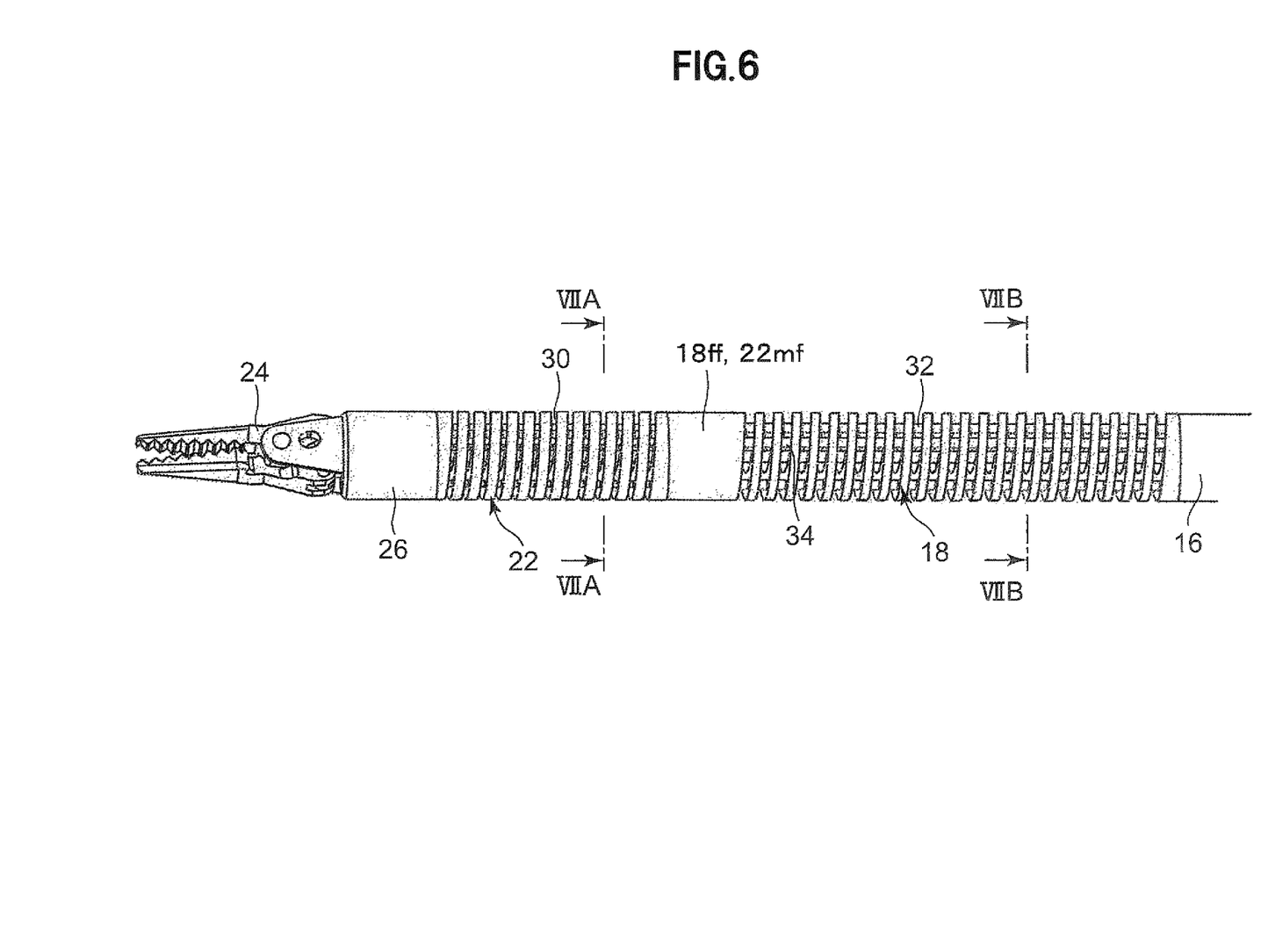
FIG. 6 is a perspective view showing a first and second joints in the embodiment shown in FIG. 1, along with a gripping unit.
Figure 7A:
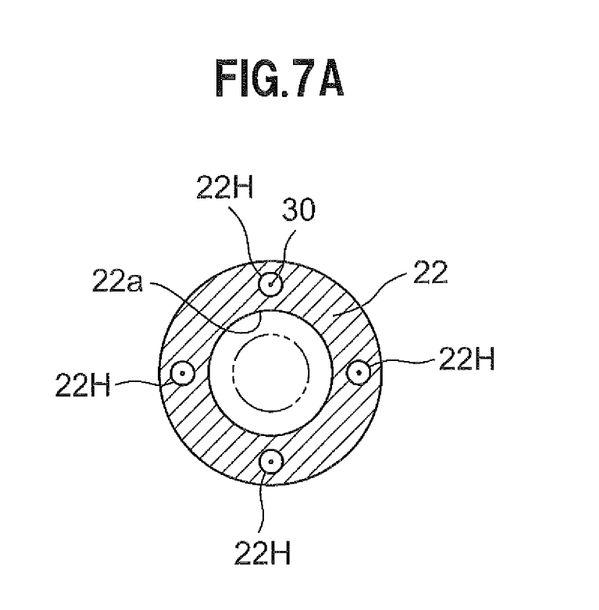
FIG. 7A is a cross-sectional view taken along a line VIIA-VIIA in FIG. 6.
Figure 7B:
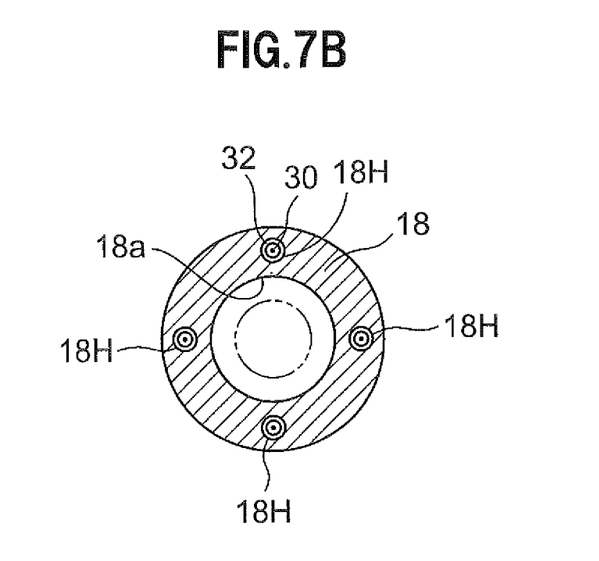
FIG. 7B is a cross-sectional view taken along a line VIIB-VIIB in FIG. 6.

In addition, as shown in FIG. 7B, the machined spring 18b is formed with throughholes 18H, where the respective tubes 32 are inserted, around the throughhole 18a at positions in association with the throughholes 18ga, 18gb. As shown in FIG. 6, the fitting hole unit 18ff of the first joint 18 is connected by the fitting cylinder 22mf of the second joint 22 with screw engagement. The fitting hole unit 18ff has a plurality of throughholes along the circumferential direction in association with a plurality of screw holes of the fitting cylinder 22mf. This allows for screwing small screws (not shown) into screw holes of the fitting cylinder 22mf via the throughholes.

The structure of the second joint 22 is a flexible structure and has a machined spring 22b as with the structure of the first joint 18. The second joint 22 has a shorter length in an axial direction, as compared to a length of the first joint 18 in an axial direction. In the second joint 22, as shown in FIG. 7A, the machined spring 22b is formed with throughholes 22H, each being inserted with only the wire 30, around a throughhole 22a, which is located in the center in a cross-sectional view, at positions in association with the grooves 18g. One end of each of the four wires 30 which runs through each of the four tubes 32 is bonded to a throughhole 22ga which communicates with a bearing housing 22BH in the second joint 22.

Figure 10:
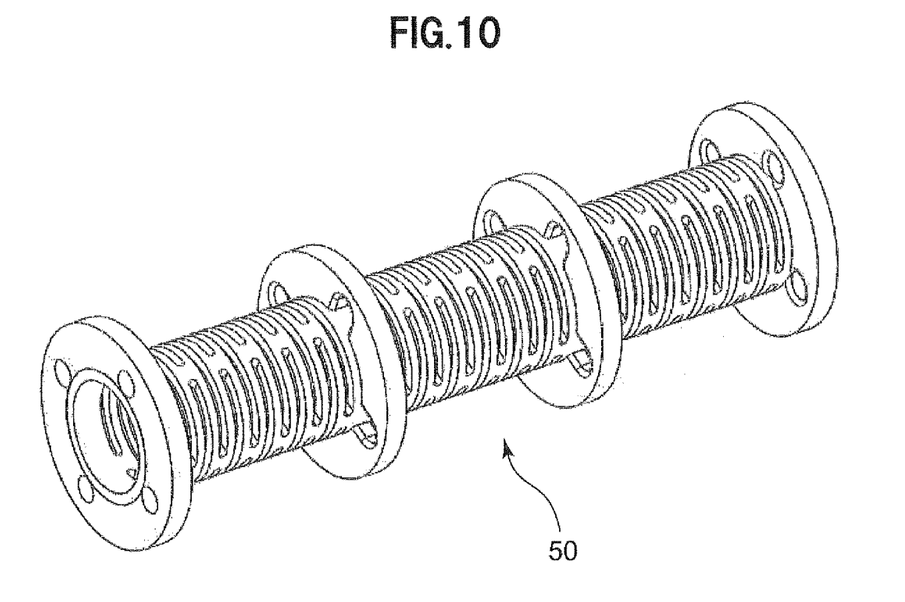
FIG. 10 is a perspective view showing another embodiment of the first and second joints in the embodiment shown in FIG. 1.

The flexible structures of the first joint 18 and second joint 22 are not limited to the above embodiment, and, for example, as shown in FIG. 10, a flexible structure 50 may be used to have slits in a β titanium tube for flexibility, and collars which are attached to several places along the periphery of the tube and provided with four guide holes for the driving tubes and wires.

Figure 8B:
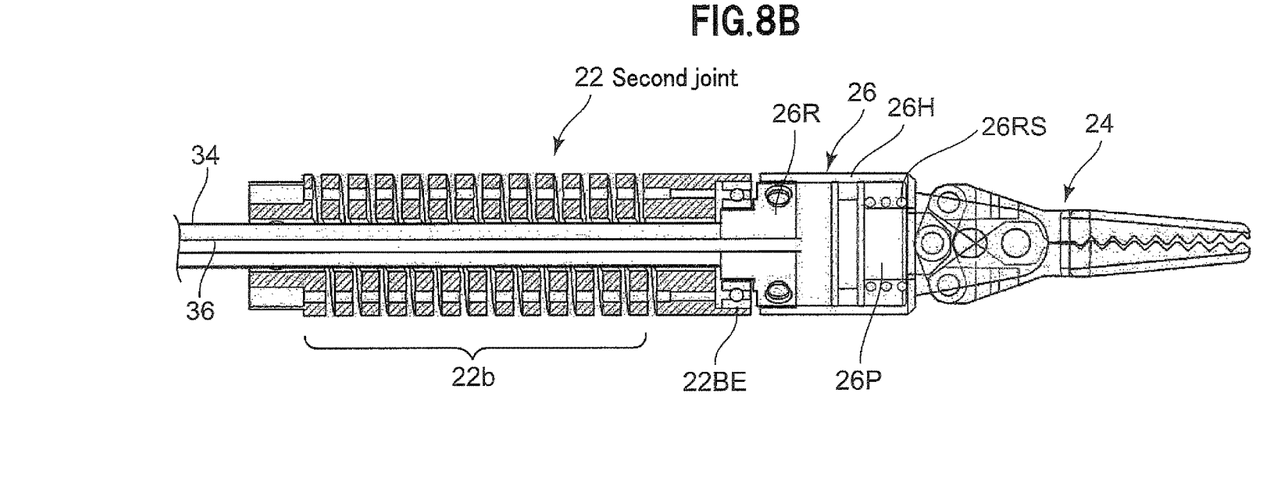
FIG. 8B is a sectional view showing a the second joint and the gripping unit shown in FIG. 1.

As shown in FIG. 8B, a rotating joint unit 26 which is connected to an end of the second joint 22 is intended to rotate a gripping unit 24, which is connected to the rotating joint unit 26, in accordance with a rotation of the flexible shaft 34. The rotating joint unit 26 includes within a housing 26H: a rotor 26R that is fixed to the inner peripheral portion of the housing 26H and transmits a rotational force of the flexible shaft 34 to the gripping unit 24; a piston 26P that makes an opening and closing mechanism of a gripper of a gripping unit 24 in a gripping state; and a return spring 26RS that returns the piston 26P to an initial state against a working air pressure, to make the opening and closing mechanism of the gripper in a non-gripping state.

The rotor 26R is rotatably supported by a ball bearing 22BE in the second joint 22 to connect to one end of the flexible shaft 34 as well as to one end of an air supply tube 36 for supplying working air into the rotating joint unit 26.

The opening and closing mechanism of the pneumatic gripper in the gripping unit 24 may be, although an illustration thereof is omitted, provided with the same mechanism as that shown in Tadano, K., Kawashima, K., Kojima, K., Tanaka, N., Development of a Pneumatic Surgical Manipulator IBIS IV, Journal of Robotics and Mechatronics, Vol. 22, No. 2, p. 179-188 (2010), for example. Such a pneumatic gripper is driven with the working air being supplied through the air supply tube which is arranged inside the flexible shaft 34.

Figure 11:
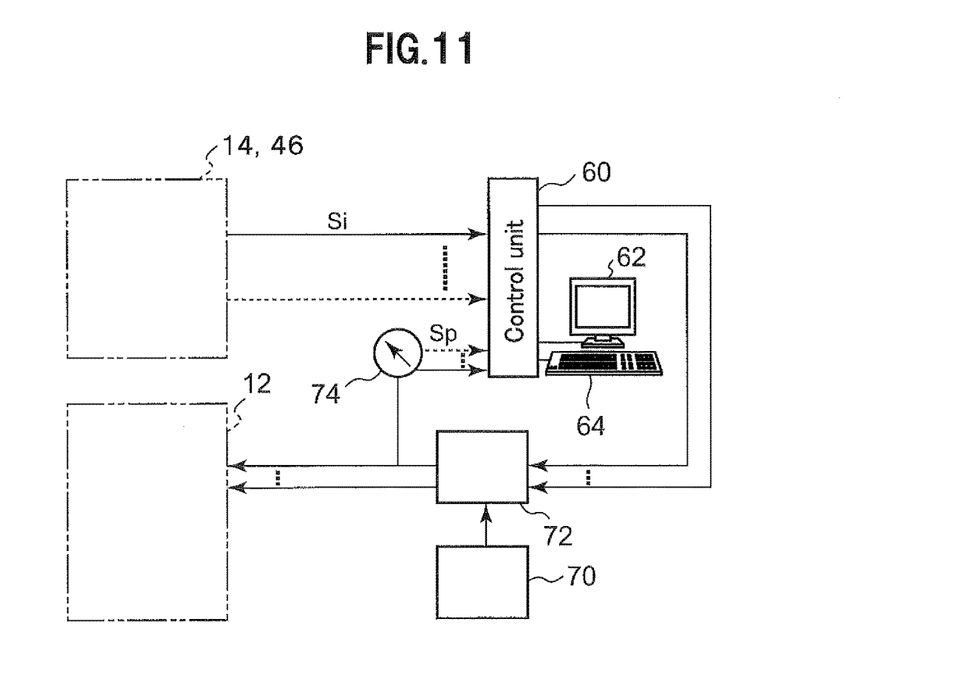
FIG. 11 is a block diagram showing a control unit included in one embodiment of a forceps system comprising the forceps manipulator according to the present invention.

In addition to the above configuration, one embodiment of the forceps system comprising a forceps manipulator according to the present invention includes a control unit 60, as shown in FIG. 11, that controls a pneumatic control circuit 72 for controlling operation of the first and second joints 18, 22 and the gripping unit 24 in the forceps manipulator as described above.

The control unit 60 is supplied with detection output signals Si from a plurality of the potentiometers 46 in the connector unit 14 as described above, and detection output signals Sp indicating pressures from respective pressure sensors 74 in the pneumatic control circuit 72 to be described later. The control unit 60 includes a storage unit for storing a predetermined program data and the like. In addition, the control unit 60 is connected with a liquid crystal display 62 as a display unit, and a keyboard 64 as an input unit.

Figure 12:
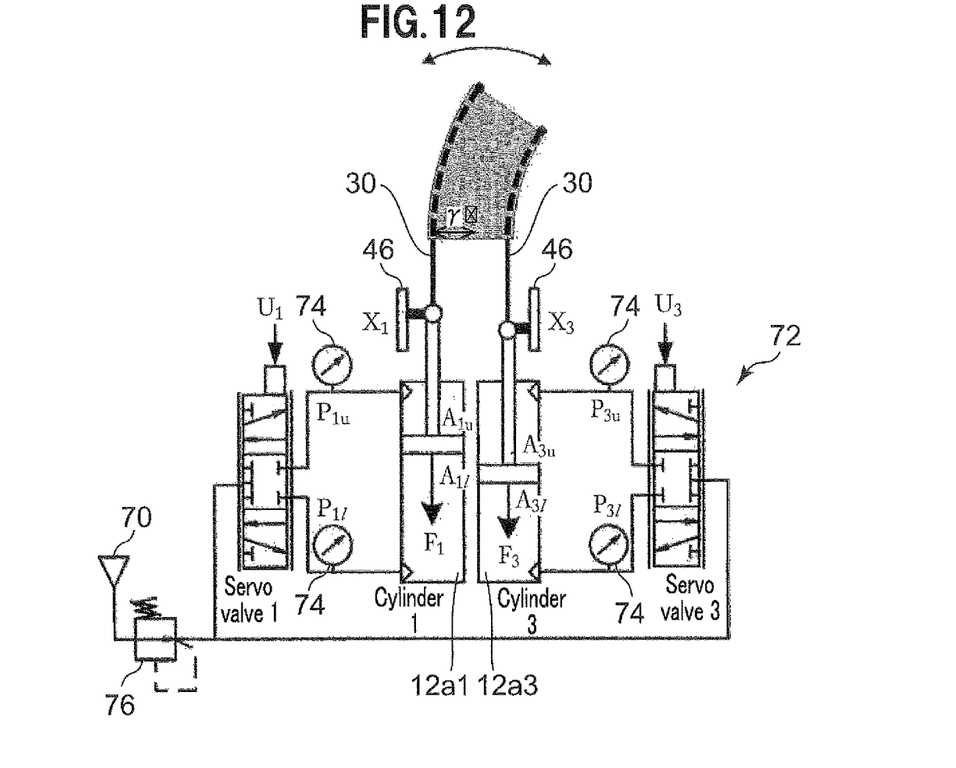
FIG. 12 is a block diagram showing a pneumatic control circuit included in one embodiment of the forceps system comprising the forceps manipulator according to the present invention.

The pneumatic control circuit 72 is provided, for example, as shown in FIG. 12, with a plurality of five-port servo valves via a pressure regulating valve 76 for an air pressure supply source 70 such as a compressor. Respective servo valves are arranged in association with the air cylinders 12a1-12a8 as described above. It should be noted that, in FIG. 12, the air cylinders 12a1 and 12a3, a servo valve 1, and a servo valve 3 are representatively shown. In this way, the air cylinders 12a1-12a4 are driven to control driving of the second joint 22 via the wires 30, and also the air cylinders 12a5-12a8 are driven to control driving of the first joint 18 via the tubes 32. Further, a vane motor 40 is controlled for controlling a rotation angle of the gripping unit 24.

The control unit 60 starts operation in accordance with a predetermined program data retrieved from the storage unit, to control positions and posture of the gripping unit 24, the first joint 18, and the second joint 22 based on the detection output signal Si and the detection output signal Sp, as well as to perform a calculation for estimating an external force vector $f_{ext}$ hat applied at the tip of a forceps to control operation of the pneumatic control circuit 72. In the control unit 60, the calculation for estimating an external force vector, to be described later, is performed in accordance with an arithmetic expression represented in a block diagram shown in FIG. 13.

Next, a description will be given of estimating an external force in the forceps system.

Figure 13:
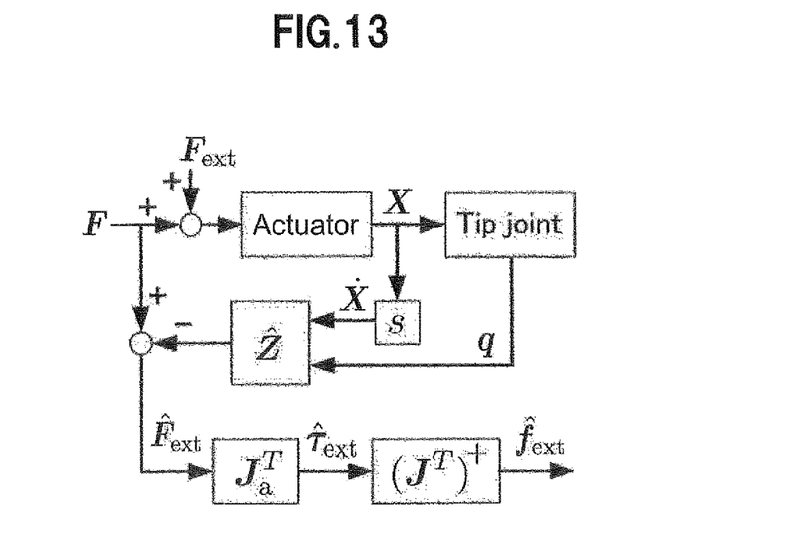
FIG. 13 is a block diagram showing an arithmetic expression calculated by the control unit shown in FIG. 11.

FIG. 13 is a block diagram of estimating an external force in the forceps system. A description will be given of a method of estimating an external force with regard to the block diagram in FIG. 13, with description of respective symbols.

Figure 15:
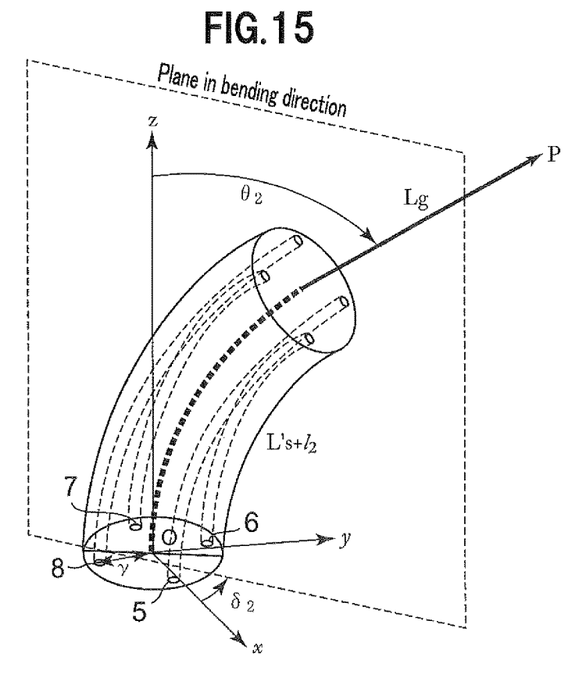
FIG. 15 is a view to be used in a description of an operation of an embodiment of the forceps manipulator according to the present invention.

F: a driving force vector of a pneumatic actuator, specifically, as follows;
　F1-F4: cylinder driving forces of the first joint,
　F5-F8: cylinder driving forces of the second joint,
　F9: a vane motor driving torque for the rotation joint.
X: displacement of the actuator, specifically, as follows;
　X1-X4: cylinder displacements for the first joint,
　X5-X8: cylinder displacements for the second joint,
　X9: a rotation angle of the vane motor for a rotating joint,
X over-dot: an actuator velocity, s means a Laplace differential operator, but actually the value is obtained by performing numerical differentiation with a computer (pseudo differential),
q: a position variable vector of a joint, in up to seven-dimensions, specifically, as follows;

$$q = [\delta_1, \theta_1, l_1, \delta_2, \theta_2, l_2, \psi]^T$$

where subscripts 1 and 2 indicate joint numbers, the definition of $\delta$, $\theta$, $l$ applied for bending are as defined in a coordinate position of the second joint shown in FIG. 15, the first joint can be the same, and $\psi$ represents an angle of the rotating joint.

For the second joint, $\delta_2$ is a direction for the joint to bend, $\theta_2$ is an angle with which the joint has bent in that direction, and $l_2$ is a variation of a joint length, where the variation $l_2$ of the joint length is a variation in the length of a longitudinal centerline of the joint, that is, a portion with dashed lines in FIG. 15. However, $\delta_2$ and $\theta_2$ need to be in a range expressed as follows;

$$-\pi \leq \delta_2 \leq \pi, \theta_2 \geq 0$$

In addition, p shows a coordinate position of the tip of the forceps, Ls is a natural length of the joint, Lg is the total length of the gripping unit and the rotating joint unit, r is the radius of a cross-sectional circle virtually formed with the driving wires arranged around the longitudinal centerline of the joint, and numerals 5-8 are driving wire numbers.

For the first joint, $\delta_1$ is a direction for the joint to bend, $\theta_1$ is an angle with which the joint has bent in that direction, and $l_1$ is a variation of a joint length. However, $\delta_1$ and $\theta_1$ need to be in a range expressed as follows;

$$-\pi \leq \delta_1 \leq \pi, \theta_1 \geq 0$$

In addition, Ls is a natural length of the joint, r is the radius of a circle virtually formed with the driving tubes arranged in a cross-sectional view, and numerals 1-4 are driving tube numbers.

Here the relationship between the q and an actuator displacement X is expressed as Equation 1.

$$X = \begin{bmatrix} X_1 \\ X_2 \\ X_3 \\ X_4 \\ X_5 \\ X_6 \\ X_7 \\ X_8 \\ X_9 \end{bmatrix} = \begin{bmatrix} -\mathcal{T}\theta_1\cos\delta_1 + \ell_1 \\ -\mathcal{T}\theta_1\sin\delta_1 + \ell_1 \\ \mathcal{T}\theta_1\cos\delta_1 + \ell_1 \\ \mathcal{T}\theta_1\sin\delta_1 + \ell_1 \\ X_1 - \mathcal{T}\theta_2\cos\delta_2 + \ell_2 \\ X_2 - \mathcal{T}\theta_2\sin\delta_2 + \ell_2 \\ X_3 + \mathcal{T}\theta_2\cos\delta_2 + \ell_2 \\ X_4 + \mathcal{T}\theta_2\sin\delta_2 + \ell_2 \\ \gamma\psi \end{bmatrix} \quad \text{(Equation 1)}$$

Note that $\gamma$ in the equation indicates a deceleration ratio (acceleration ratio) from the vane motor to the rotating joint. Next, Equation 1 can be modified as follows with respect to the joint position q.

$$q = \begin{bmatrix} \delta_1 \\ \theta_1 \\ \ell_1 \\ \delta_2 \\ \theta_2 \\ \ell_2 \\ \psi \end{bmatrix} = \begin{bmatrix} \tan^{-1}\left(\frac{X_2 - X_4}{X_1 - X_3}\right) \\ \frac{1}{2r}\sqrt{(X_1 - X_3)^2 + (X_2 - X_4)^2} \\ (X_1 + X_2 + X_3 + X_4)/4 \\ \tan^{-1}\left(\frac{(X_6 - X_2) - (X_8 - X_4)}{(X_5 - X_1) - (X_7 - X_3)}\right) \\ \frac{1}{2r}\sqrt{\{(X_5 - X_1) - (X_7 - X_3)\}^2 + \{(X_6 - X_2) - (X_8 - X_4)\}^2} \\ \frac{\{(X_5 - X_1) + (X_6 - X_2) + (X_7 - X_3) + (X_8 - X_4)\}}{4} \\ X_9/\gamma \end{bmatrix}$$

(Equation 2)

Z hat: an actuator driving-force vector in an inverse-dynamics model for implementing a desired joint position and velocity, and this is a 9-dimensional vector. Here, the Z hat may be divided into respective joints: model $Z_1$ (4-dimensional vector) of the first joint, model $Z_2$ (4-dimensional vector) of the second joint, and model $Z_r$ (1-dimensional vector) of the rotating joint. That is, Z hat can be expressed as follows.

$$\hat{Z} = \begin{bmatrix} Z_1 \\ Z_2 \\ Z_r \end{bmatrix}$$

(Equation 3)

Each component of Equation 3 is composed of terms pertinent to mechanical impedances (elastic force, frictional force, inertial force, and the like) against operation of the respective actuators;

$F_{ext}$, $F_{ext}$ hat: vectors of external force components in the cylinder driving force and the driving torque of vane motor, respectively, expressed as a nine-dimensional vector including rotation; these are generated by the forceps receiving an external force at the tip to drive the actuator backward; it should be noted that a symbol with a hat is meant to be an estimated value by calculation, $\tau_{ext}$ hat: an external force component of a torque and a translational force against joint position coordinates q ($\delta_1$, $\theta_1$, $l_1$, $\delta_2$, $\theta_2$, $l_2$, $\psi$), $f_{ext}$ hat: an external force applied to the forceps at the tip, expressed herein as a six-dimensional vector of three degrees of freedom in the translational force and three degrees of freedom in the torque, $J_a^T$: a transformation matrix from $F_{ext}$ to $\tau_{ext}$; $J_a$ is a Jacobian from a joint velocity q over-dot to an actuator velocity X over-dot, obtained by performing time differenciation on Equation 1 and organizing the results, $(J^T)^+$: a transformation matrix from $\tau_{ext}$ to $f_{ext}$; is a Jacobian from a joint velocity q over-dot to a velocity p over-dot and an angular velocity vector ω of the forceps on edge.

Figure 14:
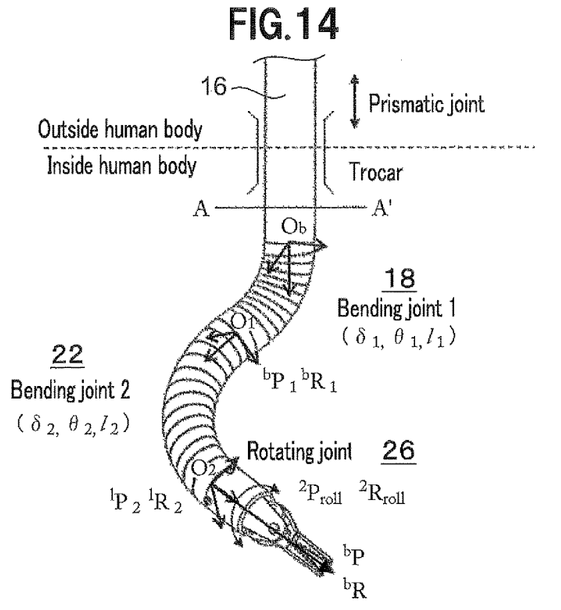
FIG. 14 is a view to be used in a description of an operation of an embodiment of the forceps manipulator according to the present invention.

A description will be given of the method of estimating an external force with reference to FIG. 14. For describing positions and posture of the first and second joints as well as the rotating joint, a reference coordinate system $O_b$ is assumed, and local coordinate systems $O_1$, $O_2$ are assumed at the axes of the first and second joints on edge. In the figure, a symbol p indicates a position (three-dimensional vector), and a symbol R indicates a posture matrix (3×3 matrix), then, for example, a description of $^b p_1$ is meant to be a position vector in $O_1$ expressed in the coordinate system $O_b$. With this arrangement, a position p and a posture matrix R of the forceps at the tip will be calculated as follows.

$$P = {}^b p = {}^b p_1 + {}^b R_1({}^1 p_2 + {}^1 R_2{}^2 p_{roll})$$  Equation 4

$$R = {}^b R = {}^b R_1 {}^1 R_2 {}^2 R_{roll}$$  Equation 5

Here, a component $J_p$, which is associated with the translation velocity, of the Jacobian J required for estimating an external force is obtained by performing time differentiation on Equation 4.

$$\dot{p} = J_p \dot{q}$$  Equation 6

Next, an angular velocity vector Ω can be obtained by calculating direction cosines of the respective rotation axis vectors with respect to the reference coordinate system for time differentiation values of angular parameters in the joint position vector q, to organize an equation in a form having a posture Jacobian $J_r$, where the time differentiation values are $\delta_1$ over-dot, $\theta_1$ over-dot, $\delta_2$ over-dot, $\theta_2$ over-dot, and $\psi$ over-dot. Here, components associated with translation velocity parameters $l_1$ over-dot and $l_2$ over-dot are assumed to be zero.

$$\Omega = J_r \dot{q}$$  Equation 7

From Equations 6 and 7, the Jacobian J can be obtained as follows.

$$J = \begin{bmatrix} J_p \\ J_r \end{bmatrix}$$  Equation 8

Incidentally, the joint position vector q as defined above have seven degrees of freedom. There can be redundant components in Equation 10, to be described later, of calculating an external force, however, if a component $l_1$ or $l_2$ in q is selectively removed, the system can be of a non-redundant and independent six degrees of freedom. A reduction of a degree of freedom for estimating an external force allows for reducing a cost and improving accuracy in inverse matrix calculations.

An estimated value $F_{ext}$ hat of a vector of components in the external force of the actuator driving force can be calculated by subtracting internal inverse dynamics Z hat of the manipulator from the driving force F of the actuator according to Equation 9, to obtain components in the external force.

$$\hat{F}_{ext} = F - \hat{Z}$$  Equation 9

The external force vector $f_{ext}$ hat applied to the forceps at the tip can be obtained according to Equation 10.

$$\hat{f}_{ext} = (J^T)^+ (J_a^T \hat{F}_{ext})$$  Equation 10

A description has been given of an embodiment using a spring as a bending unit, but the bending unit is not limited thereto. Other than this, a hollow object processed to have slits so as to be flexibly bendable, or the like can be employed as a bending unit. A description has been given of an embodiment using a potentiometer as a detecting unit for cylinder positions, but the detecting unit is not limited thereto. Other than this, an encoder or the like can be employed as a detecting unit.

A description has been given of an embodiment using an air cylinder as a driving force generator, but the driving force generator is not limited thereto. Other than this, an electric motor, a hydraulic cylinder, an oil hydraulic cylinder, or the like can be employed as a driving force generator.

A description has been given of an embodiment using a pressure sensor as a measuring device for driving forces, but the measuring device for driving forces is not limited thereto. Other than this, a method of directly mounting a force sensor on the manipulator can be employed as a measuring device for driving forces.

An embodiment according to the present invention adopts a flexible shaft for driving the rotating joint at the tip to allow for avoiding interference with the bending joint in both the kinematics and the dynamics. An embodiment of the forceps manipulator according to the present invention has seven degrees of freedom (five degrees of freedom (two degrees of freedom in bending×2 and one degree of freedom in rotating) added with stretching direction of bending joint×2)), which are effective for estimating an external force, within a human body to allow for estimated calculation of an external force having six degrees of freedom, i.e., three axes of a translation force and three axes of a torque, using only the joints within the human body.

As motions outside the human body are not used for estimating an external force, a constraint by a trocar at an inserting portion and resistances such as those caused by wires linked to the forceps manipulator do not affect dynamics of the joint. Then, the forceps manipulator has the advantage of allowing for estimating an external force always accurate even in any arrangement situation.

The invention claimed is:

1. A forceps system comprising:
   a forceps manipulator that is configured to include:
   a rotating joint unit configured to rotate a gripping unit having a forceps;
   a plurality of flexible joints, each having three degrees of freedom, that are respectively provided with throughholes along the axial direction and connected to the rotating joint unit;
   wires and tubes that are connected to the plurality of joints;
   a plurality of potentiometers configured to detect amounts of movement of the wires and tubes;
   a plurality of pressure sensors configured to detect pressures for driving air cylinders which are connected to the plurality of joints via the wires and tubes; and
   a driving unit configured to drive the rotating joint unit via flexible driving-force transmitting members which are respectively inserted into the throughholes of the plurality of joints; and
   a control unit configured to control the driving unit of the forceps manipulator so as to control posture of the gripping unit, wherein
   the gripping unit, the rotating joint unit, and the driving-force transmitting members are rotated about an axis in the axial direction.

2. The forceps system according to claim 1, wherein the control unit is configured to estimate external forces acting on the forceps manipulator.

3. The forceps system according to claim 2, wherein the control unit is configured to use signals from the plurality of potentiometers and the plurality of pressure sensors to estimate the external forces which cause the plurality of joints to be deformed.

4. The forceps system according to claim 1, wherein the plurality of joints are configured with respective machined springs.

5. A forceps manipulator comprising:
   a rotating joint unit configured to rotate a gripping unit having a forceps;
   a plurality of flexible joints, each having three degrees of freedom, that are respectively provided with throughholes along the axial direction and connected to the rotating joint unit;
   wires and tubes that are connected to the plurality of joints;
   a plurality of potentiometers configured to detect amounts of movement of the wires and tubes;
   a plurality of pressure sensors configured to detect pressures for driving air cylinders which are connected to the plurality of joints via the wires and tubes; and
   a driving unit configured to drive the rotating joint unit via flexible driving-force transmitting members which are respectively inserted into the throughholes of the plurality of joints, wherein
   the gripping unit, the rotating joint unit, and the driving-force transmitting members are rotated about an axis in the axial direction.

* * * * *